United States Patent [19]

Edenbaum et al.

[11] Patent Number: 4,655,210

[45] Date of Patent: Apr. 7, 1987

[54] FOAM BANDAGE

[75] Inventors: Martin I. Edenbaum, Princeton Junction, N.J.; Borys Rybalka, Philadelphia, Pa.

[73] Assignee: Seton Company, Newark, N.J.

[21] Appl. No.: 819,686

[22] Filed: Jan. 17, 1986

[51] Int. Cl.$^4$ ............................................. A61L 15/00
[52] U.S. Cl. .................................................. 128/156
[58] Field of Search ......................................... 128/156

[56] References Cited

U.S. PATENT DOCUMENTS

| | | | |
|---|---|---|---|
| 4,460,369 | 7/1984 | Seymour | 128/156 |
| 4,484,574 | 11/1984 | DeRusha | 128/156 |
| 4,545,372 | 10/1985 | Lauritzen | 128/156 |

Primary Examiner—Gregory E. McNeil
Attorney, Agent, or Firm—Webb, Burden, Robinson & Webb

[57] ABSTRACT

A disposable bandage, and a process for manufacturing it, which is prepared from a single sheet or strip of liquid permeable, flexible thermoplastic hydrophilic foam. The process includes coating the entire surface of one side of a foam sheet or strip with a layer of porous pressure sensitive adhesive, positioning wound release material in the area of the sheet or strip intended for wound contact, covering the same side of the laminate with a suitable release liner and heat compressing the laminate except at the locus of the wound release material. The foam bandage so produced includes both a resilient absorbent pad and thin but absorbent adhesive-coated tabs. Optionally, the bandage may have a moisture vapor permeable, moisture impermeable skin thereon, to provide a water- and bacteria-proof protective outer layer for the foam bandage.

19 Claims, 2 Drawing Figures

FOAM BANDAGE

FIELD OF THE INVENTION

The present invention relates to disposable bandages for both minor and major skin wounds and irritations and, more particularly, relates to disposable bandages prepared from a single sheet of polyurethane foam.

BACKGROUND OF THE INVENTION

Over-the-counter disposable bandages have enjoyed popularity for decades. The use of such bandages is widespread in the first-aid treatment of minor skin wounds such as abrasions and accidental incisions. Moreover, certain features have been added to these bandages, during their development, to increase comfort to the user; these features include wound release materials, perforations in the adhesive tabs, and the like. The resulting products have gained substantial consumer acceptance.

Unfortunately, these disposable bandages continue to present disadvantages both to the manufacturer and the consumer. The most popular bandages include a perforated plastic sheet or strip, the sides of which are ordinarily coated with a perforate pressure sensitive adhesive composition on their inner surfaces, having a wound covering pad (typically gauze) positioned in and adhered to the center of the strip or sheet. The wound facing surface of the pad is treated or laminated so as to prevent the pad from adhering to the wound. Release material coated strips are placed over the adhesive tabs and the bandage itself is then packaged and sterilized for sale or use. This process, although it results in a commercially acceptable product, requires several manufacturing steps and a number of component materials, thus preventing the simple, low-cost manufacture of the article.

Although the difficulties in manufacturing these bandages are substantial, the most significant disadvantages are those to the ultimate user of the bandage. Because the gauze pads lint, they deposit dust and/or fiber into the open wound. The gauze pad itself has so little thickness, compounded by a total lack of resilience, that the pad provides to the wound site little if any protection from contusion or other pressure trauma. This same gauze pad is likewise deficient in that it can absorb and hold only small amounts of medicaments or fluids such as wound exudates. In addition, despite improvements in pressure sensitive adhesives in recent years, conventional disposable bandages continue to cause pain and tissue trauma upon removal, particularly in sensitive areas such as the interdigital skin of the hands. Finally, the overwhelming majority of these disposable bandages are used on the fingers. When the adhesive tabs of these bandages are wrapped and overlapped about a finger, the tabs lose most or all of their moisture vapor permeability because the perforations in the overlapping tabs seldom if ever align to permit moisture vapor transmission. As a result, the skin covered by overlapping adhesive tabs macerates beneath a plastic vapor barrier.

Even the most recent developments in the disposable bandage art have failed to rectify the most significant of these problems. For example, the "Unitary Adhesive Bandage," disclosed in U.S. Pat. No. 4,530,353, is manufactured from a sheet of heat fusible fibrous material, such as a nonwoven batt, which is folded at the center into a 3-layer pad and calendered at the sides to form tabs. The pad is then provided with a wound release surface, the tabs are coated with a hot melt adhesive and the bandage as a whole is fitted with release strips.

Unfortunately, the resulting product—like its predecessor disposable bandages—introduces fibrous batt type fibers and lint into the area of the wound, provides calendered adhesive coated thermoplastic tabs having no apparent absorbency or moisture vapor permeability, and covers the area of the wound with a comparatively non-resilient fibrous batt material. Furthermore, only the tab portions of the bandage may be coated with the hot melt adhesive, necessitating careful application of the adhesive to specified portions of the bandage during manufacture. In addition, the manufacture of the bandage requires both the preparation of a triple fold in the batt material and the precise calendering of the bandage—before application of the adhesive—to heat seal *both* the tab portions of the bandage and a tiny section of each side of the folded pad. Without this precise calendering, the structural integrity of the bandage might be well be lost during manufacture, marketing or use.

In view of all of the patented or otherwise known bandage products and designs, therefore, a need remains for an improved disposable bandage which may be manufactured from a single flat sheet, without folding, may be fabricated without gauze, batts, or other fibrous linting materials, and may be coated with a single adhesive layer over its entire surface, for ease of manufacture. Such a product would additionally demonstrate improved absorbency over known fibrous materials, as well as superior protective resilience in the area of the wound and ready permeability to moisture *and* moisture vapor in both the pad area and the adhesive tabs of the bandage.

BRIEF DESCRIPTION OF THE INVENTION

As an article to meet these needs, the present invention is a disposable bandage, and a process for manufacturing it, which is prepared from a single sheet or strip of liquid permeable, flexible, hydrophilic thermoplastic foam. The process includes coating the entire surface of one side of a foam sheet or strip with a layer of porous pressure sensitive adhesive, positioning wound release material in the area(s) of the sheet or strip intended for wound contact, covering the same side of the laminate in entirety with a suitable release liner and heat compressing the laminate except in the area of the pad. Numerous foam bandages may be prepared from the same sheet of foam by cutting the selectively heat compressed laminate into individual bandages. The foam bandage so produced provides both a resilient absorbent pad and thin but absorbent adhesive-coated tabs. Furthermore, the single layer of porous pressure sensitive adhesive adheres the wound release material to the pad during and after manufacture, adheres the tabs to the skin during use, and permits the ready passage of fluid (i.e., water, serum, wound exudate, or moisture) or moisture vapor into the absorbent areas of the bandage. Optionally, the bandage may be prepared from a foam sheet having a moisture vapor permeable, moisture impermeable skin thereon, or a similar skin may be cast onto the prepared bandage; in either case, the skin provides a water- and bacteria-proof protective outer layer for the foam bandage described herein.

DETAILED DESCRIPTION OF THE INVENTION

Figure 1:
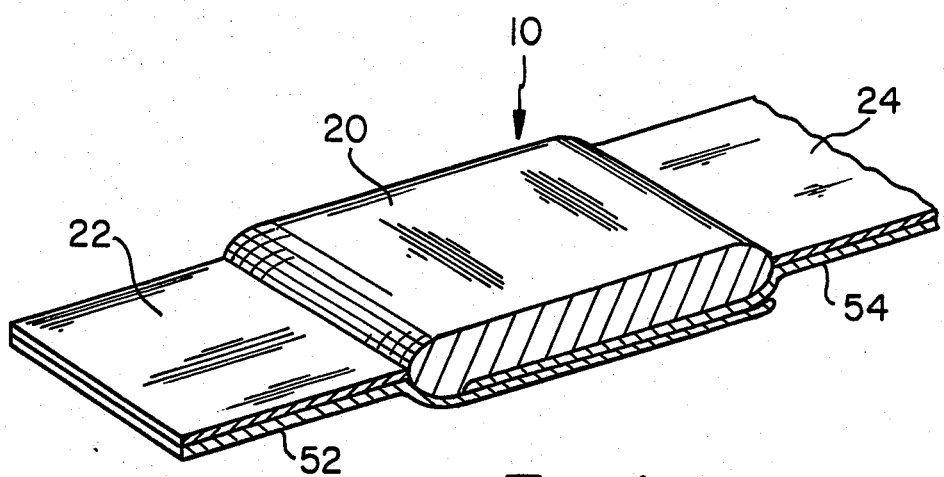
FIG. 1 illustrates a perspective view of the foam bandage 10, having a pad 20, first and second tabs 22 and 24, and release strips 52 and 54 thereon.

As described above, the process for preparing the present foam bandage includes coating one side of a polyurethane foam sheet with a layer of porous pressure sensitive adhesive, positioning wound release material and release liner adjacent the adhesive, and heat compressing the entire laminate except in the area(s) of the wound-covering pad(s). The equipment and methods for accomplishing these laminating steps are well-known in the art, as explained below. The selection of the particular materials for incorporation in the laminate and the resultant foam bandage requires special care, however, and so the foam bandage is best described by identifying first those component materials suitable for use therein.

I. Liquid Permeable, Flexible Foams

The liquid permeable, flexible foams suitable for use in the present invention are those which demonstrate significant, and preferably substantial, hydrophilicity. These hydrophilic compositions may be prepared by any means known in the art, i.e., foaming prepolymers by means of the addition of chemical or physical blowing agents. Accordingly, hydrophilic polyurethane compositions may be prepared either by foaming isocyanate-capped prepolymers by the addition of water, or by frothing aqueous dispersion of fully reacted polyurethane polymers to entrap chemically inert gases therein. These foam compositions must be prepared, of course, with the understanding that any types or amounts of additives, introduced to confer or improve hydrophilicity or other characteristics of the foam, will not result in medically unacceptable cytotoxicity in the ultimate composition so produced. For example, the following surfactants may be used to enhance hydrophilicity in the preparation of hydrophilic foam compositions for use in the present invention: sorbitan trioleate; polyoxyethylene sorbitan oleate; polyoxyethylene sorbitan monolaureate; polyoxyethylene lauryl ether; polyoxyethylene stearyl ether; fluorochemical surfactants such as Zonyl FSN by E. I. du Pont and Fluorad FC 170C by 3M, and block copolymer condensates of ethylene oxide and propylene oxide with propylene glycol, such as the PLURONIC surfactants available from BASF Wyandotte.

In addition, the compositions suitable for use in the present invention are those which are thermoplastic, i.e., which reversibly soften upon heating. Preferably, the compositions will soften and become tacky, or at least self-adherent, between 225° and 300° F., although compositions may be used which soften between 200° and 350° F. Accordingly, the thermoplastic compositions incorporated into the invention demonstrate thermal stability at ordinary room temperatures.

Finally, the foam compositions suitable for use in the present invention are those which may be cast or skived into low-density sheets. In particular, sheets formed from these compositions must have a density between 4 and 20 lbs/ft$^3$, preferably between 7 and 13 lbs/ft$^3$, and more preferably between 10 and 12 lbs/ft$^3$. The low density of the foam contributes both to the lightweight absorbency of the foam bandage and the low cost of the materials necessary in the manufacture thereof. The low density foams may be open-celled or partially open-celled, as long as the foams are liquid permeable in contrast to the rigid impermeable closed-cell foams.

The most widely available foams for the purpose of the present invention are the polyurethanes, including those which result from foaming isocyanate-capped prepolymers and those prepared by frothing aqueous polyurethane dispersions. For the purpose of the present invention, however, foam sheets prepared by mechanically frothing, casting and curing aqueous polyurethane dispersions are preferred. The polyurethanes having utility for this preferred purpose are, accordingly, those recognized in the art as ionically water dispersible. These dispersions are in contrast with the emulsified isocyanate copolymers such as those disclosed in U.S. Pat. No. 2,968,575, which are prepared and dispersed in water with the aid of detergents under the action of powerful shearing forces. The emulsified polyurethanes have the disadvantage that a detergent must be used to form the emulsion and such detergent is usually retained in the cured polyurethane, thus seriously detracting from the overall physical and chemical properties of the final product.

The preferred system for preparing aqueous ionic polyurethane dispersions is to prepare polymers that have free acid groups, preferably carboxylic acid groups, covalently bonded to the polymer backbone. Neutralization of these carboxyl groups with an amine, preferably a water soluble mono-amine, affords water dilutability. Careful selection of the compound bearing the carboxylic group must be made because isocyanates, the reactive group employed most often in the generation of urethane linkages, are generally reactive with carboxylic groups. However, as disclosed in U.S. Pat. No. 3,412,054, incorporated herein by reference, 2,2-hydroxymethyl-substituted carboxylic acids can be reacted with organic polyisocyanates without significant reaction between the acid and isocyanate groups as a result of the steric hindrance of the carboxyl by the adjacent alkyl groups. This approach provides the desired carboxy-containing polymer with the carboxylic groups being neutralized with the tertiary mono-amine to provide an internal quaternary ammonium salt and, hence, water dilutability.

Suitable carboxylic acids and, preferably, the sterically hindered carboxylic acids, are well-known and readily available. For example, they may be prepared from an aldehyde that contains at least two hydrogens in the alpha position which are reacted in the presence of a base with two equivalents of formaldehyde to form a 2,2-hydroxymethyl aldehyde. The aldehyde is then oxidized to the acid by procedures known to those skilled in the art. Such acids are represented by the structural formula:

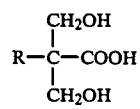

wherein R represents hydrogen, or alkyl of up to 20 carbon atoms, and preferably, up to 8 carbon atoms. A preferred acid is 2,2-di(hydroxymethyl)propionic acid.

The polymers with the pendant carboxyl groups are characterized as anionic polyurethane polymers. Further in accordance with the present invention, however, an alternate route to confer water dilutability is to use a cationic polyurethane having pendant amino groups. Such cationic polyurethanes are disclosed in U.S. Pat. No. 4,066,591, incorporated herein by reference, and particularly, in Example XVIII. In the context of the present invention, however, anionic polyurethane dispersions are preferred.

The polyurethanes useful in the practice of the invention more particularly involve the reaction of di- or polyisocyanates and compounds with multiple reactive hydrogens suitable for the preparation of polyurethanes. Such diisocyanates and reactive hydrogen compounds are more fully disclosed in U.S. Pat. No. 3,412,054 and No. 4,046,729. Further, the processes to prepare such polyurethanes are well recognized as exemplified by the aforementioned patents. In accordance with the present invention, therefore, aromatic, aliphatic and cyclo-aliphatic diisocyanates or mixtures thereof can be used in forming the polymer. Such diisocyanates, for example, are tolylene-2,4-diisocyanate; tolylene-2,6-diisocyanate; meta-phenylene diisocyanate; biphenylene-4,4'-diisocyanate; methylene-bis-(4-phenol isocyanate); 4,4-chloro-1,3-phenylene diisocyanate; naphthylene-1,5-diisocyanate; tetramethylene-1,4-diisocyante; hexamethylene-1,6-diisocyanate; decamethylene-1,10-diisocyanate; cyclohexylene-1,4-diisocyanate; isophorone diisocyanate and the like. Preferably, the arylene and cycloaliphatic diisocyanates are used in the practice of the invention.

Characteristically, the arylene diisocyanates encompass those in which the isocyanate group is attached to the aromatic ring. The most preferred isocyanates are the 2,4 and 2,6 isomers of tolylene diisocyanate and mixtures thereof, due to their reactivity and ready availability. The cycloaliphatic diisocyanates used most advantageously in the practice of the present invention are 4,4'-methylene-bis(cyclohexyl isocyanate) and isophorone diisocyanate.

Selection of the aromatic or aliphatic diisocyanates is predicated upon the final end use of the particular material. As is well recognized by those skilled in the art, the aromatic isocyanates may be used where the final product is not excessively exposed to ultraviolet radiation, which tends to yellow such polymeric compositions. The aliphatic diisocyanates, on the other hand, may be more advantageously used in exterior applications and may have less tendency to yellow upon exposure to ultraviolet radiation. Although these principles form a general basis for the selection of the particular isocyanate to be used, the aromatic diisocyanates may be further stabilized by well-known ultraviolet stabilizers to enhance the final properties of the polyurethane product. In addition, antioxidants may be added in art recognized levels to improve the characteristics of the final dispersions. Typical antioxidants are the thioethers and phenolic antioxidants such as 4,4'-butylidine-bis-meta cresol and 2,6-ditert-butyl-para-cresol.

The isocyanate is reacted with the multiple reactive hydrogen compounds such as diols, diamines or triols. In the case of diols or triols, they are typically either polyalkylene ether or polyester polyols. A polyalkylene ether polyol is the preferred active hydrogen containing polymeric material for formulation of the polyurethane. The most useful polyglycols have a molecular weight of 50 to 10,000 and, in the context of the present invention, the most preferred is from about 400 to about 7,000 with the higher molecular weight polyols conferring proportionately greater flexibility upon the polymer. The desired elastomeric behavior will generally require approximately 0.5–80 percent by weight of a long chain polyol (i.e. 700 to 2,000 eq. wt.) in the polymer.

Examples of the polyether polyols are, but not limited to, polyethylene ether glycol, polypropylene ether glycol, polytetramethylene ether glycol, polyhexamethylene ether glycol, polyoctamethylene ether glycol, polydecamethylene ether glycol, polydodecamethylene ether glycol, and mixtures thereof. Polyglycols containing several different radicals in the molecular chain, such as, for example, the compound $HO(CH_2OC_2H_4O)_nH$ wherein n is an integer greater than 1, can also be used.

The polyol may also be a hydroxy terminated or hydroxy pendant polyester which can be used instead of or in combination with the polyalkylene ether glycols. Exemplary of such polyesters are those formed by reacting acids, esters or acid halides with glycols. Suitable glycols are polymethylene glycols, such as ethylene, propylene, tetramethylene or decamethylene glycol; substituted methylene glycols such as 2,2-dimethyl-1,3-propane diol, cyclic glycols such as cyclohexane diol and aromatic glycols. Aliphatic glycols are generally preferred when flexibility is desired. These glycols are reacted with aliphatic, cycloaliphatic or aromatic dicarboxylic acids or lower alkyl esters for ester-forming derivatives to produce relatively low molecular weight polymers, preferably having a melting point of less than about 70° C. and a molecular weight comparable to those set forth above for the polyalkylene ether glycols. Acids suitable for use in preparing such polyesters are, for example, phthalic, maleic, succinic, adipic, suberic, sebacic, terephthalic and hexahydrophthalic acids and the alkyl and halogen substituted derivatives of these acids. In addition, a polycaprolactone terminated with hydroxyl groups may also be used.

When used herein, "ionic dispersing agent" means an ionizable acid or base capable of forming a salt with the solubilizing agent. These "ionic dispersing agents" are amines and preferably are water soluble amines such as triethylamine, tripropylamine, N-ethyl piperidine, and the like; also, acid and preferably water soluble acids such as acetic, propionic, lactic, and the like. Naturally, an acid or amine will be selected contingent upon the solubilizing group pendant on the polymer chain.

In forming the polyurethanes useful in the practice of the invention, the polyol and a molar excess of diisocyanate are reacted to form isocyanate terminated polymer. Although suitable reaction conditions and reaction times and temperatures are variable within the context of the particular isocyanate and polyol utilized, those skilled in the art well recognize the variations. Such skilled artisans recognize that reactivity of the ingredients involved requires the balance of reaction rate with undesirable secondary reactions leading to color and molecular weight degradation. Typically, the reaction is carried out with stirring at about 50° C. to about 100° C. for about 1 to 4 hours. To provide pendant carboxyl groups, the isocyanate terminated polymer is reacted with a molar deficiency of dihydroxy acid for 1 to 4 hours at 50° C. to 120° C., to form isocyanate prepolymer. The acid is desirably added as a solution, for example, in N-methyl-1,2-pyrrolidone or N-N-dimethylformamide. The solvent for the acid will typically be no more than about 5 percent of the total charge in order to minimize the organic solvent concentration in the polyurethane composition. After the dihydroxy acid is reacted into the polymer chain, the pendant carboxyl groups are neutralized with an amine at about 58°–75° C. for about 20 minutes, and chain extension and dispersion are accomplished by addition to water with stirring. A water soluble diamine may be added to the water as an additional chain extender. The chain extension involves the reaction of the remaining isocyanate groups with water to form urea groups and to polymerize further the polymeric materials, with the result that all the isocyanate groups are reacted by virtue of the addition to a large stoichiometric excess of water.

The dispersion viscosity is generally in the range of from 10 to 1000 centipoise. Useful solutions of polyurethane in organic solvents, by contrast, generally have viscosities of several thousand centipoise, ranging as high as 50,000 centipoise when the solution contains about 20 to 30 percent by weight polyurethane.

Suitable polyurethane dispersions contain, moreover, about 50 to 75 percent by weight polyurethane solids in dispersion, said solids preferably having a carboxyl content between about 92 and 98 meq per each 100 grams thereof. The preferred polyurethane concentration is 55 to 70 percent by weight and the most preferred concentration is 65 percent by weight polyurethane solids in dispersion.

Particle size, as a useful measure of stability, may be measured by light scattering. Useful dispersions having non-settling characteristics will have particles of a diameter of less than 5 microns.

Particularly useful polyurethane dispersions include the non-crosslinked polyurethane compositions recited in U.S. Pat. No. 4,171,391, incorporated herein by reference. The polyurethane dispersions most preferred for use in the present invention, however, are those available from Witco Chemical Company under the trade designation Witcobond ® W-290H; these dispersions yield foams which demonstrate inherent hydrophilicity, even in the absence of surfactants. The Witcobond ® W290H dispersions contain 65 percent by weight anionic polyurethane solids having particulate diameters less than 5 microns.

In order to froth the aqueous ionic polyurethane dispersions in accordance with the present invention, the dispersions are first admixed with a stearic acid salt and a small amount of an aziridine crosslinking agent. The salt of stearic acid may be selected from the group consisting of aluminum stearate, ammonium stearate, calcium stearate, potassium stearate and sodium stearate. The aziridine crosslinking agent may be any known aziridine crosslinking agent wherein the agent has monofunctional or polyfunctional aziridine activity due to the incorporation therein of ethyleneimine, propyleneimine, butyleneimine or derivatives thereof. Preferably, the aziridine selected is the polyfunctional aziridine preparation of proprietary formula, sold under the trademark XAMA ®-7, which contains 6.35 to 6.95 meq/g aziridine content and has an aziridine functionality of approximately 3.3. The XAMA ®-7 polyfunctional aziridine has a viscosity of 1200 to 2000 centipoise at 25° C., further has a density of 1.185 g/cc at 25° C., and is completely miscible with water, acetone, methanol, chloroform and benzene.

The admixture is prepared by combining between 80 and 120 parts by weight of an aqueous ionic polyurethane dispersion, prepared as described above, with between 0.5 to 1.5 parts by weight of XAMA ®-7 polyfunctional aziridine and between 1 and 9 parts by weight of a 33 percent aqueous or nonaqueous dispersion of the stearate salt. Different amounts and concentrations of other stearate and aziridine preparations may be substituted in reactive equivalent amounts. To this admixture may be added additional ingredients and reactive or nonreactive additives, such as surfactants, as desired.

On a laboratory scale, the dispersion, stearate and aziridine may be admixed in a Hobar mixer; an Oaks or other industrial frothing mixer is suitable for full scale production. After initial admixing of the polyurethane dispersion, the stearate and the aziridine, the mixture is frothed, by agitation and/or inert gas injection, to yield a frothed admixture which has very fine, uniform bubbles and which is suitable for immediately casting and curing. Although the froth may be cast by other means, the froth is particularly suited to the knife-casting techniques for preparing foam sheet materials. Preferably, therefore, the liquid froth is cast upon a release surface, such as silicone coated release paper, and coated to the desired thickness with, for example, a Gardner knife. The release paper-frothed layer is then passed through an oven to dry and cure the foam. Temperatures of 225° F. to 275° F. are suitable for drying and curing the foam, and the limited inclusion of the aziridine compound ensures the thermoplasticity of the foam sheet subsequent to curing.

II. Adhesives

A number of adhesive compositions are suitable for use in the present invention. The adhesive must be, however, film-forming, noncytotoxic within medically acceptable limits, and porous in its ultimate film form. (The term "porous" signifies the presence of a plurality of discontinuities or apertures.) Suitable adhesive preparations therefore include, for example, solutions or emulsions of acrylic adhesive resin, blends of butadiene-acrylonitrile copolymers with resins such as oil-soluble, heat-hardening phenol-formaldehyde resins, two-step thermosetting phenolic resin compositions, coumarone-indene resins, polyterpine resins and the like; polychloroprene combined with heat-hardening phenol-formaldehyde resins, rosin-phenol resins, vinyl alkyl ether polymer based adhesives, thermoplastic styrene-butadiene block polymer rubbers mixed with resins such as those described, and other such adhesive compositions.

Porosity may be conferred upon these adhesive compositions by means known in the art. For example, a solution of the adhesive may be frothed in a Hobart or Oakes mixer, followed by the casting and curing of the resultant froth to yield a porous film. Because the solvent removal necessary with conventional solvent systems ordinarily creates problems of compliance with environmental safety regulations, however, porous adhesive films prepared from aqueous dispersions or emulsions of dispersible adhesive resins are popular in the industry and are preferred for use in the present invention. These dispersions or emulsions are frothed, cast and cured, in the same manner as the solvent system adhesives to yield porous pressure sensitive adhesive films. These films are adequately porous as long as they are readily permeable, i.e., penetrable within 90 seconds, to liquid water, serum, and ordinary wound exudates.

Particularly useful pressure sensitive adhesive emulsions include those sold in association with the mark Rhoplex ®, by Rohm and Haas Company. These Rhoplex ® adhesives includes Rhoplex N-560, Rhoplex N-580, Rhoplex N-582, Rhoplex N-619, Rhoplex N-1031 and Rhoplex LC-67. These preparations are particularly well suited to the preparation of the present adhesive films because, for example, they require no additional tackifying resins and yield films having excellent resistance to delamination under wet conditions. In addition, porous films prepared from these adhesive emulsions do not lose tack or porosity under the application of heat, i.e., up to 400° F. Other adhesive films may accordingly be substituted for the films prepared from the Rhoplex emulsions, as long as the films do not lose tack or porosity at temperatures up to and including 400° F.

III. Structure, Function and Manufacture

Referring now to the drawings, and initially to FIG. 1, two or more of the above-described polyurethane foams and adhesive formulations are incorporated into tue preferred embodiment of the foam bandage 10 having a pad 20, a first tab 22 and a second tab 24, which are backed, respectively, by the first and second release strips 52 and 54.

Figure 2:
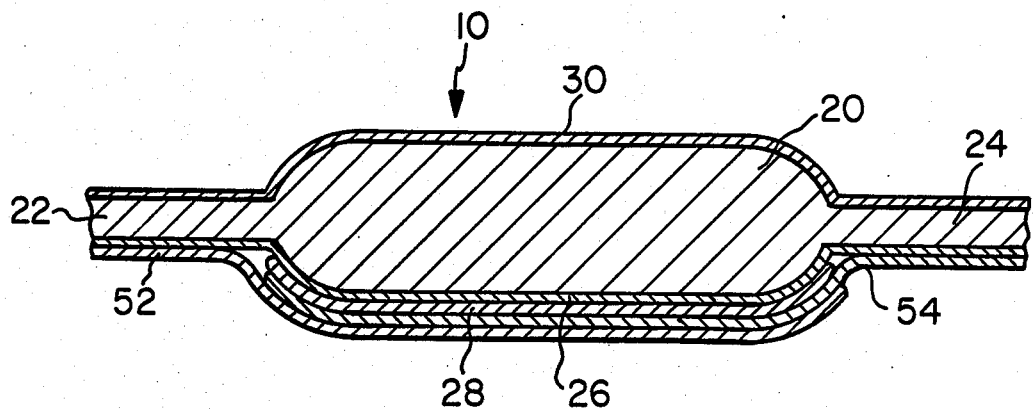
FIG. 2 illustrates a side elevational view of the pad 20, having layers of porous pressure sensitive adhesive 26 and wound release material 28 laminated thereto beneath the release strips 52 and 54.

Referring now to FIG. 2, the porous pressure sensitive adhesive layer 26 extends the length of the foam bandage 10, and is shown adjacent to the foam layer of both the pad 20 and the first and second tabs 22 and 24. A wound release liner layer 28 adheres to the adhesive layer 26 in the area of the pad 20, and the first and second release strips 52, 54 cover the entire bandage, contacting the adhesive layer 26 only in the areas of the first and second tabs 22 and 24. A moisture vapor permeable skin 30, which is moisture vapor permeable yet moisture and bacteria impermeable, is illustrated on the external surface of the foam bandage 10.

The preferred embodiment of the foam bandage, as illustrated in the FIGS., functions generally as do other disposable bandages, and is applied to the skin in the conventional manner. The pad 20 does not lint, however, when brought adjacent an irritation or wound, and the sole porous pressure sensitive adhesive layer 26 ensures gentle adherence of the foam bandage to the skin during use. Furthermore, both the first and second tabs 22 and 24 and the pad 20 are constructed in part of a liquid permeable, flexible hydrophilic polyurethane foam, and the tabs and the pad therefore both provide ready absorption and transfer of fluids and moisture vapor from the area of the wound or irritation. The moisture permeable hydrophilic foam tabs 22, 24, exclusive of the moisture vapor permeable skin 30 thereon, furthermore tend to wick fluids away from the pad 20 when the pad approaches saturation prior to the tabs. Moreover, the ready transfer of moisture vapor though the foam bandage 10 remains unaffected even when the bandage is wrapped and overlapped, i.e., around a finger, because the overlapped moisture vapor permeable layers continue to define a moisture vapor permeable structure. Accordingly, the moisture vapor permeable skin 30 provides a bacterial barrier for the wound without causing skin maceration on the otherwise moisture and moisture vapor permeable foam bandage 10.

The foam bandage according to the preferred and alternate embodiments of the invention may be manufactured in a number of ways, each of which is simple, straightforward and cost effective. A low-density liquid permeable, flexible polyurethane foam sheet is first prepared as described above. The porous pressure sensitive adhesive layer is then adhered to the foam sheet by direct casting, reverse-roll, transfer coating or other methods known in the art. A wound release inner layer is then positioned in those areas of the foam sheet/adhesive film laminate that are intended for wound contact, i.e., pad areas. These wound release materials include the Delnet ® (Hercules) and Cerex ™ (DuPont) materials and are net-like, nonabsorbent materials which permit free passage of fluids. (Delnet ® wound release material, in particular, is a high density perforated polyethylene sheet material which has good adherence to pressure sensitive adhesive resins but functions as a release surface to coagulated serum.) The resulting laminate, in which wound release material is present only in the areas intended for wound contact, accordingly contains three layers which individually and collectively permit the free passage and absorption of fluids, serum and wound exudate.

Over the entire foam/adhesive film/wound release liner layer is then positioned a suitable release material. These release materials include release papers known in the art along with any other sheet materials having a release coating on one side thereof. Typical release papers are prepared by slightly impregnating and completely coating the surface of the paper or other material with a composition which resists the adhesion of ordinary adhesives. A number of such release coatings are known in the art, among them being cured silicones, cured blends of alkyd resins and urea-formaldehyde resins and stearato chromic chloride (e.q., "Quilon"). The release material may be positioned solely over the adhesive areas free from wound release material or may be overlapped across the designated pad area of the bandage in the characteristic configuration typical of prior art disposable bandages.

The resultant laminate is then heat compressed in those areas of the laminate intended as the first and second tabs 22, 24; the intended area of the pad 20 is left uncompressed. This heat compression is preferably effected by heated rollers. If the laminate is first cut into strips having a width the intended length of each individual bandage, the side portions of each strip may be heat compressed with smooth heated rollers; if the entire sheet is heat compressed at once, a heated roller having a grid pattern thereon corresponding to the desired bandage structure is used. The rollers are heated to between 200° and 350° F., and preferably are heated to between 225° and 300° F. If desired, only one of two cooperating rollers need be heated, or a single heated roller may substitute for two cooperating rollers under suitable manufacturing conditions. In any event, the heat compression should proceed to heat compress the laminate to a predetermined thickness by adjusting one or more rollers to the corresponding gap, allowing for any shrinkage in the heat-compressed polymer as it cures. Within the scope of this invention, the foam/adhesive film/wound release layer/release liner laminate may be heat compressed to any thickness as long as the compressed portions of the laminate remain both moisture and moisture vapor permeable. Preferably, however, the compressed portions of the foam/adhesive film laminate will have less than the thickness, and more preferably less than half of the thickness, of the uncompressed pad areas thereof.

Optional elements may be added to the subject foam bandage without altering the nature of the invention. First, the thermoplastic foam may have a moisture vapor permeable, moisture impermeable skin, such as a urethane skin, on the outside thereof, as is present in the preferred embodiment of the invention; this urethane skin opposes the wound release material and porous adhesive layers intended for contact with the human skin surface. The moisture vapor permeable, moisture impermeable skin may either be cast onto the foam sheet or the ultimate prepared foam bandage, or may be prepared as a substrate onto which the thermoplastic foam is initially cast and cured. Second, additional optional absorbent materials may be positioned between the porous pressure sensitive adhesive layer and the wound release material in the area of the pad by, for example, interposing a non-linting cellulose or other absorbent layer narrower than the foam pad between the porous pressure sensitive adhesive layer and the wound release material. As a result, the entire absorbent layer and the edges of the wound release material layer are affixed to the thermoplastic foam by means of one layer of porous pressure sensitive adhesive. Unlike the optional outer moisture vapor permeable skin of the foam bandage, of course, this optional absorbent material must be positioned within the laminate prior to the positioning of the wound release material and release liners, and before the heat compression of the assembled laminate.

Following heat compression, the laminate is permitted to cool, at which time the thermoplastic foam either reverts to a stable solid or becomes thermoset by the further heat activation of a crosslinking compound (i.e., remaining unreacted aziridine) present in the foam. After cooling, the laminate is cut into individual disposable foam bandages and the bandages are packaged and sterilized by means known in the art.

Bandage dimensions and thicknesses may be adjusted to suit specific applications. Both strip- and island-type bandages may be prepared in accordance with the present invention. Likewise, larger disposable bandages in the configuration of general medical or surgical dressings may be prepared and used in home-health or hospital care of more serious wounds and conditions. The hydrophilicity of the thermoplastic polyurethane foam, and the ease of manufacture of the foam bandage as a whole, make it suitable and cost effective for use in all first-aid, medical or surgical applications.

The following Examples are illustrative of the foam bandage of the present invention, and the process for preparing it.

EXAMPLE I

Five hundred parts by weight of Witcobond ® W-290H aqueous polyurethane dispersion, containing 62 percent by weight anionic polyurethane solids, were admixed, at slow speed in a Hobart mixer, with 25 parts by weight 33 percent aqueous ammonium stearate, five parts by weight XAMA ®-7 polyfunctional aziridine, fifteen parts by weight Lexaine C (a cocamidopropyl betaine viscosity builder available from Inolex Chemical Co., Philadelphia, Pa.) and 25 parts by weight of Pluronic ® L-62 surfactant. The resulting admixture demonstrated a viscosity of 3000 centipoise.

The above admixture was mixed in the Hobart mixer for 1 minute at low speed, 1 minute at medium speed, 2 minutes 30 seconds at high speed and 2 minutes at low speed. The admixture thus frothed was then coated, at 0.170" gap, over a 1 mil thick cured urethane skin which demonstrated a moisture vapor transmission rate of 800 g/m$^2$/24 hours. The cast foam/urethane skin so produced was cured by a 10 minute application of heat in a 250° F. oven. The resulting foam layer had a thickness of 110 mils and was firmly adhered to the 1 mil thick urethane skin.

EXAMPLE II

A porous pressure sensitive adhesive film was prepared by admixing 50 parts by weight Rhoplex ® N-560 pressure sensitive adhesive emulsion and 50 parts by weight Rhoplex ® N-580 pressure sensitive adhesive emulsion. The admixed emulsions were frothed in a Hobart mixer for 2 minutes at low speed, 2 minutes at medium speed, and 3 minutes 30 seconds at high speed. The resultant frothed emulsions were cast, using a Gardner knife set at 0.002", onto silicone resin coated release paper. The cast adhesive was dried into a film by heating for 8 minutes in a 300° F. oven. Samples of the porous pressure sensitive adhesive film demonstrated ready permeability both to liquid water and to a simulated serum containing water, electrolytes and albumin. The porous pressure sensitive adhesive film so produced measured 1.5 mils in thickness.

EXAMPLE III

A sheet of the urethane skin/polyurethane foam laminate of Example I was laminated, by its foam side, to a porous adhesive sheet prepared in accordance with Example II; lamination was accomplished by the adhesive transfer method. The resulting laminate was placed, adhesive layer up, on a large horizontal work surface and the release paper was removed. Leaving a one-inch margin on two opposing sides of the laminate, one inch wide strips of Delnet ® wound release material were placed lengthwise along the entire width of the sheet, with two inch spaces between each strip. Two inch wide strips of silicone resin coated release paper were then positioned along the entire width of the sheet, resting atop both the adhesive and wound release material layers. The first two inch wide strip was positioned at the left edge of the sheet, and the second strip placed to overlap the first two inch strip by one inch. The third two inch strip was positioned immediately adjacent to—but not overlapping—the second strip and the fourth strip overlapped the third by one inch. This process continued until the entire skin/foam/adhesive film laminate was covered with alternately overlapped strips of release paper. The laminate thus covered was run through smooth hard rubber rollers, at room temperature, to bond the layers into a cohesive sheet.

The resultant sheet was then cut into strips at each line of the sheet along which the release paper did not overlap. A plurality of laminated strips resulted, each of which had a width of three inches and a central area of overlapped release paper measuring one inch wide. Two sets of two cooperating one inch wide steel rollers were heated to 250° F. and were positioned parallel each other, one inch apart. The cooperating rollers were each adjusted to a 15 mil gap. The laminated strips were then passed through the set of four rollers at a rate which permitted a dwell time of six seconds. The sides of the laminated strip were accordingly heat compressed into approximately a 15 mil thickness. The strips were cooled at room temperature for 30 minutes and were then sliced into individual foam bandages having the appearance of the foam bandage illustrated in FIG. 1.

Although the invention has been described with reference to specific materials and specific processes, the invention is to be limited only insofar as is set forth in the accompanying claims.

We claim:

1. A foam bandage, comprising a laminate having a liquid permeable foam layer and a liquid permeable porous pressure sensitive adhesive layer, and having a wound release material adjacent said adhesive for separating said adhesive from a tissue healing area, and securement means associated with said laminate to attach the laminate.

2. The foam bandage according to claim 1, wherein said area of said laminate intended for wound contact defines a pad.

3. The foam bandage according to claim 2, wherein said foam layer and said adjacent porous pressure sensitive adhesive layer exclusive of said pad are heat compressed laminates having a thickness less than said pad.

4. The foam bandage according to claim 3, wherein said porous pressure sensitive adhesive layer is permeable to liquid water and serum.

5. The foam bandage according to claim 3, wherein said foam layer is a thermoplastic polyurethane foam.

6. The foam bandage according to claim 5, wherein said thermoplastic polyurethane foam is hydrophilic.

7. The foam bandage according to claim 6, wherein said hydrophilic thermoplastic polyurethane foam has a moisture vapor permeable, moisture impermeable skin thereon opposite said adhesive layer.

8. The foam bandage according to claim 7, wherein said moisture vapor permeable, moisture impermeable skin is a urethane skin.

9. The foam bandage according to claim 4, wherein said wound release material is permeable to liquid water and serum.

10. The foam bandage according to claim 9, wherein said porous pressure sensitive adhesive layer is at least partially covered with a release liner.

11. The foam bandage according to claim 10, wherein an absorbent layer is positioned between said porous pressure sensitive adhesive layer and said wound release material.

12. The foam bandage according to claim 11, wherein said porous pressure sensitive adhesive layer and said wound release material are each entirely covered with a release liner.

13. A method for preparing a foam bandage, comprising:
  (a) selecting a low density liquid permeable foam sheet;
  (b) adhering a porous pressure sensitive adhesive layer, which is permeable to liquid water and serum, to said low density foam sheet to form a laminate;
  (c) positioning a wound release material in the area of said laminate intended for wound contact to separate the adhesive from a tissue healing area; and
  (d) heat compressing the entire sheet thus produced except in the area of said wound release material.

14. The method according to claim 13, wherein step (a) further comprises the step of:
  (a) selecting a low density foam sheet having a moisture vapor permeable, moisture impermeable skin thereon.

15. The method according to claim 13, wherein step (a) further comprises the step of:
  (a) selecting a low density hydrophilic thermoplastic polyurethane foam sheet having a moisture vapor permeable, moisture impermeable urethane skin thereon.

16. The method according to claim 13, wherein step (c) further comprises the step of:
  (c) partially covering the area of said laminate intended for wound contact with an absorbent material, positioning a wound release material over the entire area of said laminate intended for wound contact, and positioning a release layer adjacent said wound release material.

17. The foam bandage according to claim 1, wherein said securement means comprises said adhesive.

18. The foam bandage according to claim 1, wherein said foam is at least partially open-celled.

19. The method according to claim 13, said foam being at least partially open-celled.

* * * * *